US006482518B1

(12) United States Patent
Short et al.

(10) Patent No.: US 6,482,518 B1
(45) Date of Patent: Nov. 19, 2002

(54) EXCIPIENT FOR THE LYOPHILIZATION OF AQUEOUS SUSPENSIONS OF MICROPARTICLES

(75) Inventors: Robert E. Short, Los Gatos; Thomas B. Ottoboni, Belmont, both of CA (US)

(73) Assignee: Point Biomedical Corporation, San Carlos, CA (US)

( * ) Notice: Subject to any disclaimer, the term of this patent is extended or adjusted under 35 U.S.C. 154(b) by 0 days.

(21) Appl. No.: 09/364,207

(22) Filed: Jul. 30, 1999

Related U.S. Application Data

(60) Provisional application No. 60/094,639, filed on Jul. 30, 1998.

(51) Int. Cl.[7] .............................. B32B 5/16; A61K 9/14
(52) U.S. Cl. ....................... 428/403; 424/489; 424/490; 424/491; 424/498; 428/407
(58) Field of Search ................................ 428/403, 407; 424/491, 489, 490, 498

(56) References Cited

U.S. PATENT DOCUMENTS

| | | | | |
|---|---|---|---|---|
| 3,939,260 A | * | 2/1976 | Lafon | 424/28 |
| 4,295,280 A | * | 10/1981 | Krupey | 34/5 |
| 4,616,047 A | * | 10/1986 | Lafon | 523/105 |
| 4,780,321 A | * | 10/1988 | Levy et al. | 424/499 |
| 4,818,542 A | * | 4/1989 | DeLuca et al. | 424/491 |
| 4,874,605 A | * | 10/1989 | Urban, Jr. et al. | 424/78 |
| 5,011,690 A | * | 4/1991 | Garvey et al. | 424/401 |
| 5,019,400 A | * | 5/1991 | Gomboltz et al. | 424/497 |
| 5,079,018 A | * | 1/1992 | Ecanow | 426/385 |
| 5,413,797 A | * | 5/1995 | Khan et al. | 424/489 |
| 5,750,142 A | * | 5/1998 | Friedman et al. | 420/450 |
| 5,882,684 A | * | 3/1999 | Schutz et al. | 424/489 |
| 6,309,569 B1 | * | 10/2001 | Farrar et al. | 264/4.1 |

FOREIGN PATENT DOCUMENTS

| WO | WO 98/29100 | 7/1998 |
|---|---|---|
| WO | WO 98/48783 | 11/1998 |

* cited by examiner

*Primary Examiner*—Hoa T. Le
(74) *Attorney, Agent, or Firm*—Fish & Richardson P.C.

(57) ABSTRACT

An excipient for lyophilizing a suspension of microparticles is provided comprising an oil-in-water emulsion of an aqueous phase and an organic phase where the organic phase has a freezing point of about or higher than the freezing point of the aqueous phase. When frozen and dried with a suspension of microparticles, the organic phase is substantially removed and a dry formulation is formed of discrete microparticles substantially free of aggregates.

15 Claims, 4 Drawing Sheets

EXCIPIENT FOR THE LYOPHILIZATION OF AQUEOUS SUSPENSIONS OF MICROPARTICLES

The priority of Provisional Application Ser. No. 60/094,639, filed Jul. 30, 1998 is claimed and its content is incorporated by reference herein in its entirety.

BACKGROUND OF THE INVENTION

Suspensions of microparticles are finding increasing application in the pharmaceutical industry for delivery of diagnostic and therapeutic agents. In some cases, it is desirable or necessary to supply a suspension of microparticles in a dry powder form that can be reconstituted to an aqueous system just prior to use. One method of drying an aqueous medium is by lyophilization by which the medium is frozen and then the water is extracted by sublimation under vacuum. If the aqueous medium contains a suspension of microparticles, these microparticles tend to cluster during the initial freezing step of the lyophilization process due to the propagation of the crystallization front. Often, the microparticles become permanently aggregated and do not redisperse when reconstituted. In applications requiring the microparticle suspension to be injected intravenously, the presence of aggregates is unacceptable because of their tendency to become trapped in the capillary bed with potentially deleterious effects.

SUMMARY OF THE INVENTION

An excipient for lyophilizing a suspension of microparticles is provided comprising an oil-in-water emulsion consisting of an aqueous phase containing suitable bulking agents, cryoprotectants, and surfactants and an organic phase wherein the organic phase has a freezing point of about or higher than the freezing point of the aqueous phase and which is substantially or completely removed during the lyophilization process. The ratio of the aqueous phase to the organic phase is typically in the range of 80:20 and 30:70 v/v. The concentration of microparticles suspended in the emulsion should be such that the number of emulsion droplets far exceeds the number of microparticles. This will insure that each microparticle is surrounded by a plethora of droplets. The emulsion droplets thus act as a protective colloid preventing direct microparticle to microparticle contact as they are clustered together into aggregates during the freezing step of the lyophilization process. The resulting aggregates would then be composed of the microparticles commingled with the frozen organic phase emulsion droplets.

During the drying steps of the lyophilization process, both the water and organic phases are extracted, leaving a dry cake derived from the aqueous phase solutes. Within the cake are suspended the microparticles surrounded by hollow voids where there previously were the frozen microbeads of the inner organic phase. Since the microparticles are separated from one another by voids, the reconstituted composition is an aqueous suspension of discrete microparticles essentially free of aggregation.

The present invention also provides a method to produce a suspension of microparticles having a lessened tendency to separate from its suspending medium by sedimentation or by creaming. Upon reconstitution the microparticle suspension becomes a purely aqueous system with a viscosity determined solely by the dissolved solutes.

DESCRIPTION OF THE PREFERRED EMBODIMENTS

Figure 1:
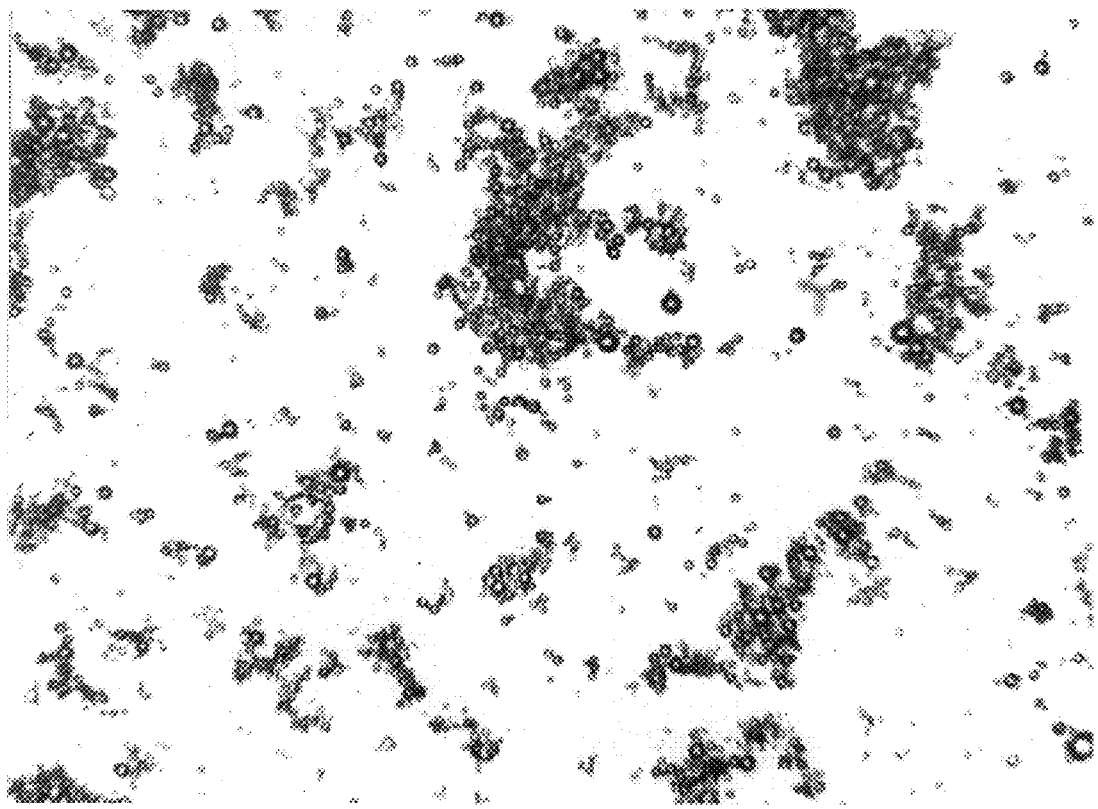
FIG. 1 is a photomicrograph of a suspension of gas-filled microparticles prepared and lyophilized in an aqueous medium in accordance with Example 1.

The excipient for lyophilizing a suspension of microparticles according to the invention comprises an oil-in-water emulsion wherein the organic phase has a freezing point of about or higher than the freezing point of the aqueous phase and can be substantially or completely removed during the lyophilization process. The organic phase will typically comprise alkanes, cycloalkanes, cycloalkanones, cycloalcohols, and the like containing at least about 6 carbon atoms and up to about 20 carbon atoms. Examples include cyclooctane, cyclohexane, cyclohexanone, n-pentadecane, n-hexadecane, cyclohexanol, and the like. The aqueous phase of the emulsion contains ingredients typically found in lyophilization excipients to provide bulking and cryoprotection such as polyethylene glycol, polyvinyl alcohol, polyvinyl pyrrolidone, dextran; sugars such as dextrose, mannitol, sucrose, lactose, trehalose, and sorbitol; amino acids such as glycine, arginine, aspartic acid; and soluble proteins such as collagen, gelatin, or serum albumin. Also included in the aqueous phase to act as the emulsifier for the inner organic phase are surfactants such as the polyoxamers (Pluronic®), polyoxyalkylene fatty acid esters (Tween®), polyoxyethylene esters (Myrj®), polyoxyethylene ethers (Brij®), and the like.

The microparticles of the suspension may be solid, porous, or a capsule comprising an outer shell and an inner wall. The microparticles need not necessarily be neutrally buoyant to insure that they remain in suspension prior to the freezing step of the lyophilization process because the relatively higher viscosity of the emulsion excipient enhances the suspension stability. The microparticles typically contain a therapeutic material such as a drug or a diagnostic material such as a gas for use as a contrast agent in echocardiography. If the reconstituted microparticle suspension is intended for intravenous injection then it is preferable that the microparticles be discrete, of a diameter range of 1–10 microns, and made from biocompatible materials such as a synthetic biodegradable polymer, a protein, or a combination of these. Examples of a synthetic biodegradable polymer include polycaprolactone, polylactide, polyglycolide, and their copolymers. Useful proteins include gelatin, serum albumin, and collagen.

To produce the emulsion excipient, a variety of devices can be used. Examples of suitable equipment include colloid mills, rotor/stator homogenizers, high pressure homogenizers, microporous membrane homogenizers, and ultrasonic homogenizers. Typically the volumetric ratio of the aqueous phase to the organic phase is in the range of 80:20 to 30:70. At ratios of around 50:50 and greater, the aqueous phase and the organic phase can simply be mixed together and then homogenized. If an emulsion of greatly enhanced viscosity is desired, the volume of the organic phase needs to be substantially greater than that of the aqueous phase. Processing of such an emulsion may then require a slow addition of the organic phase into the aqueous phase during emulsification to prevent phase inversion to a water-in-oil emulsion. The viscosity of an emulsion formulation can be increased by increasing the inner phase to outer phase ratio. At ratios exceeding one, the viscosity of the emulsion is typically far greater than that of the viscosity of the continuous phase alone. A more viscous medium is advantageous in increasing the stability of a microparticle suspension. This allows for a longer "shelf life" of the medium prior to lyophilization.

Droplet size of the organic inner phase of the emulsion, for best results, should be at most on the same order as that of the microparticles of the suspension, preferably in the range of 1–10 microns. More preferred are droplet sizes on the order of 0.2–2 microns.

Once the emulsion is produced, the microparticles are then added to the emulsion and thoroughly dispersed. The number of microparticles in the suspension is determined by the intended application so long as their numeric concentration is far less than the numeric concentration of droplets of the inner organic phase so that each microparticle is surrounded by emulsion droplets with a low probability that microparticles are in direct contact with one another.

The emulsion excipient containing the microparticles in suspension is placed into appropriate containers and then lyophilized. The lyophilization cycle typically includes a freezing step, a primary drying step, and a secondary drying step. The temperature and the duration of the freezing step is selected to insure that all components of the emulsion excipient are completely frozen. This can be determined by an examination of the freezing point of the organic phase and a study of the freezing points of the eutectic mixtures in the aqueous phase. Typically, this is below −40° C. The primary drying step involves the sublimation of the liquid components of the emulsion in vacuo. The temperature of the drying step must be high enough to provide a sufficient rate of sublimation of the liquid components yet low enough to insure that all components of the emulsion excipient remain frozen. Since sublimation provides considerable cooling to the product, temperatures for the drying step are generally much higher than those for the freezing step. Drying temperatures in the range of −30° C. to −5° C. are typical.

After primary drying, residual amounts of liquid which could not be removed by sublimation are removed by a secondary drying step. To remove these residuals, the temperature is raised to near ambient or higher. After the lyophilization cycle is complete, a dry white cake remains derived from the solutes of the aqueous phase which provides a rigid suspending medium for the microparticles. Reconstitution of the lyophilized cake with aqueous medium results in a suspension of discrete substantially unaggregated microparticles.

The following examples are provided by way of illustration and are not intended to limit the invention in any manner.

COMPARATIVE EXAMPLE 1

Microcapsules having a bilayered gelatin/caprolactone shell encapsulating a liquid organic core were suspended in an aqueous solution containing 5% polyethylene glycol-3400, 1.5% glycine, and 0.1% poloxamer 407 at a concentration of approximately $5 \times 10^8$ microparticles/ml. Microcapsule diameters ranged between 1 to 10 microns with a volumetric median diameter of approximately 4 microns. Aliquots of 2 ml of the suspension were lyophilized in 10 ml vials using an FTS Systems Dura-Stop Freeze Dryer. After lyophilization, water content of the resulting cake was measured to be less than 0.5%. The cake was then reconstituted with 2 ml deionized water and agitated for 30 seconds using a vortex mixer. Microscopic inspection revealed that only a small minority of microcapsules were discrete while the majority were in large aggregates. FIG. 1 is a photomicrograph of the reconstituted microcapsule suspension which shows the high degree of aggregation. Note that the liquid-filled microcapsules of the preparation become gas-filled after lyophilization.

EXAMPLE 2

An emulsion containing 6 parts by volume of an aqueous outer phase composed of 5% polyethylene glycol-3500, 2.1% glycine, and 0.5% poloxamer 188 and 4 parts by volume of cyclooctane as the inner phase was prepared using an Omni rotor/stator homogenizer. Microparticles similar to those described in Example 1 were suspended in the emulsion. Microcapsule concentration in the emulsion excipient was approximately $5 \times 10^8$ microcapsules/ml. Aliquots of 3 ml of the suspension were lyophilized in 10 ml vials and the resulting cake was reconstituted with 2 ml deionized water and agitated by hand.

Figure 2:
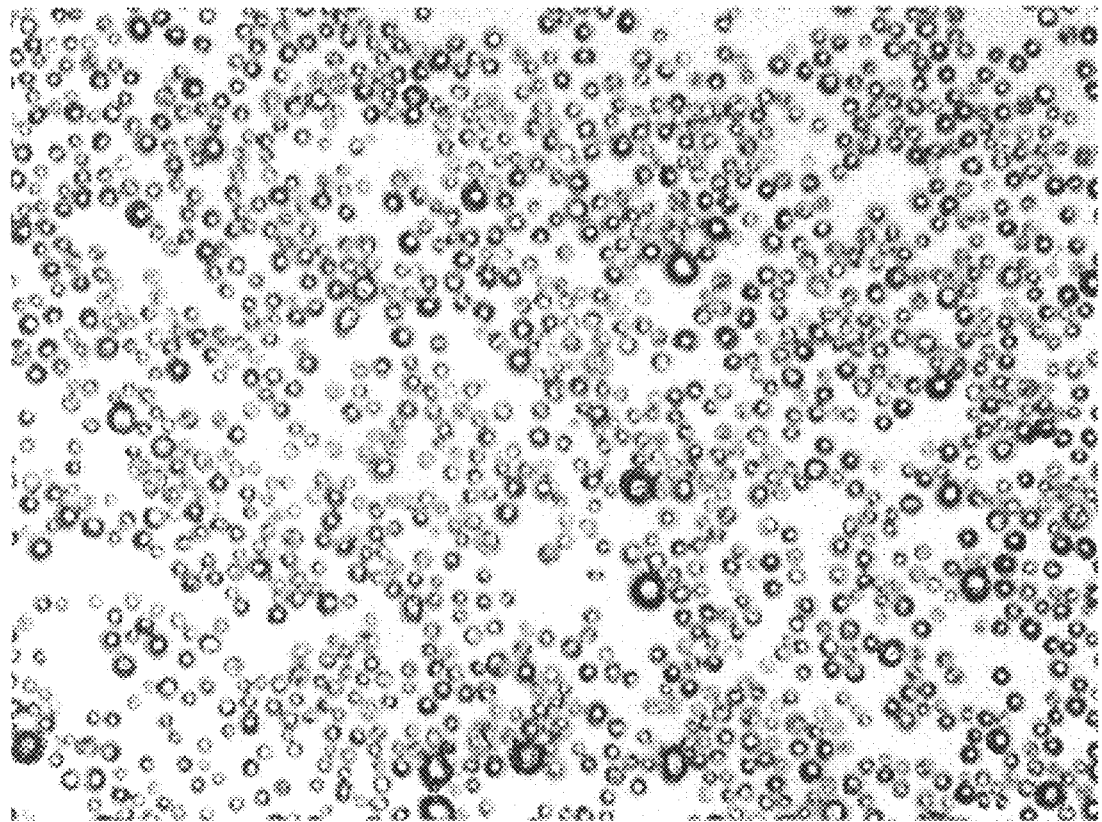
FIG. 2 is a photomicrograph of a suspension of gas-filled microparticles prepared and lyophilized in an emulsion medium in a manner similar to example 2.

Microscopic inspection revealed that substantially all the gas-filled microcapsules were discrete. FIG. 2 is a photomicrograph of the reconstituted microcapsule suspension showing a near total absence of microparticle aggregation.

EXAMPLE 3

Figure 3:
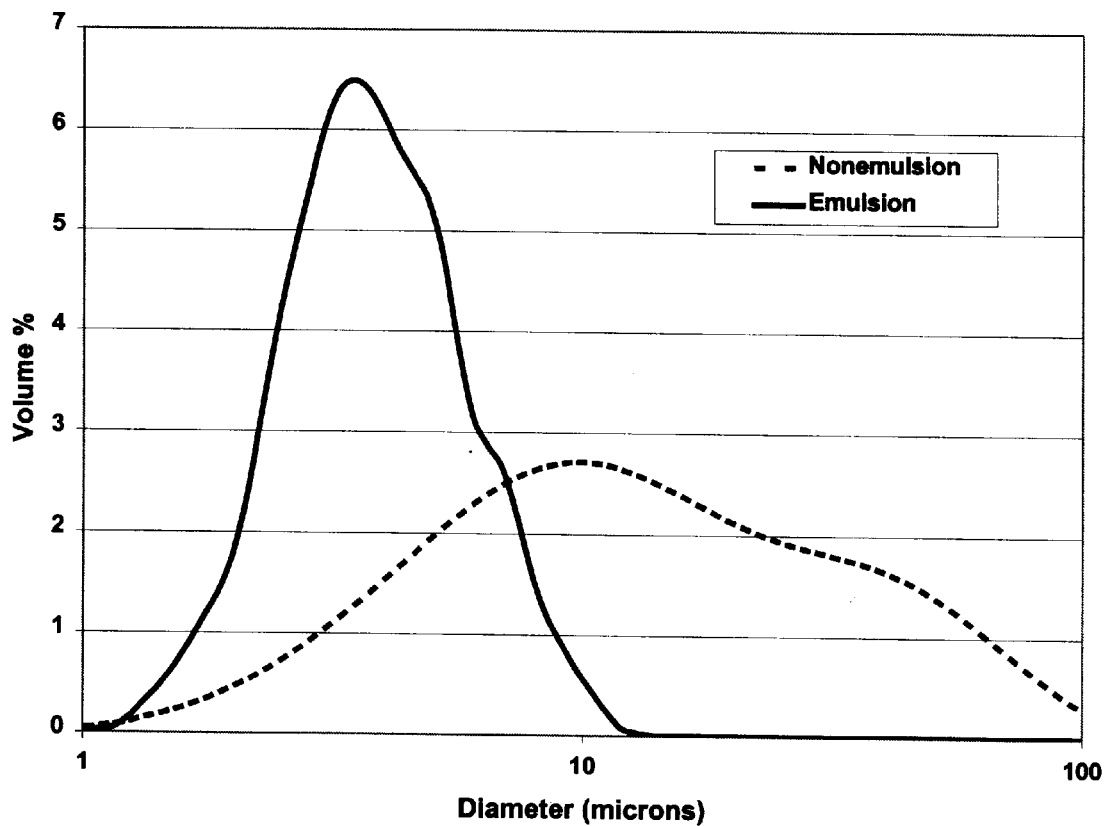
FIG. 3 is a comparison of the particle size distribution of reconstituted gas-filled microparticles lyophilized in an aqueous excipient formulation and an emulsion excipient formulation.

A reconstituted microcapsule suspension prepared in a manner similar to Example 1 and a reconstituted microcapsule suspension prepared in a manner similar to Example 2 were tested to determine their particle size distribution using a Malvern Mastersizer Micro Particle Size Analyzer. This instrument measures the diffraction pattern of light passing through a suspension of microparticles. Software then analyzes the measurement by applying Fraunhofer scattering theory to generate results and display a histogram of the diameters of the microparticles being tested. The microcapsules in both tested samples were essentially identical in size and character. FIG. 3 compares the volumetric particle size histogram of the two suspensions. The histogram of the reconstituted microparticle suspension prepared from the emulsion excipient has a much narrower span than does the reconstituted microparticle suspension prepared from the 100% aqueous excipient. Also, the peak diameter of the microparticle suspension prepared from the 100% aqueous excipient is on the order of 10 microns where the peak diameter of the suspension prepared from the emulsion excipient is approximately 4 microns. Since the Malvern Particle Size Analyzer cannot distinguish a single particle from an aggregate of particles, the results provide a good representation of the difference in the degree of aggregation between the two preparations.

EXAMPLE 4

An emulsion containing 6 parts by volume of an aqueous outer phase composed of 3% glycine, 0.3% human serum albumen, and 0.5% poloxamer 188 and 4 parts by volume of cyclooctane as the inner phase was prepared using a Virtis VirSonic Sonicator at a setting of 6 for approximately 30 seconds. Microparticles similar to those described in Example 1 were suspended in the emulsion. Microcapsule concentration in the emulsion excipient was approximately $5 \times 10^8$ microcapsules/ml. Aliquots of 3 ml of the suspension were lyophilized in 10 ml vials and the resulting cake was reconstituted with 2 ml deionized water and agitated by hand. Microscopic inspection revealed that substantially all the gas-filled microcapsules were discrete.

Figure 4:
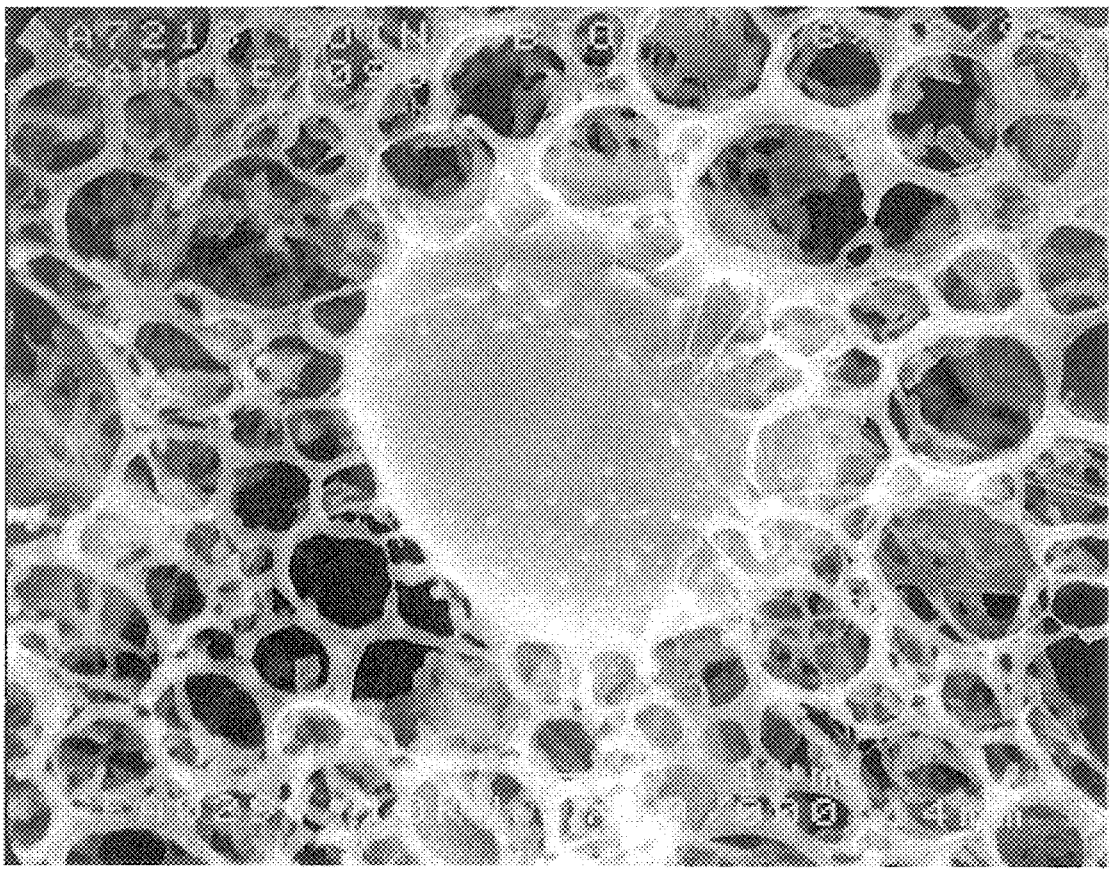
FIG. 4 is a scanning electron micrograph of the lyophilized cake of a gas-filled microparticle suspension prepared from an emulsion excipient formulation.

FIG. 4 is a scanning electron micrograph of a portion of the lyophilized cake. Clearly visible is a microcapsule suspended within a network of spherical voids which are remnants of the organic inner phase of the emulsion excipient.

What is claimed is:

1. A composition comprising:
    a suspension of microparticles in an excipient comprising an oil-in-water emulsion of an aqueous phase and an organic phase wherein the organic phase has a freezing point of about or greater than the freezing point of said aqueous phase and said organic phase is substantially removable from the suspension of microparticles by lyophilization.

2. The composition according to claim 1 wherein the volumetric ratio of said aqueous phase to said organic phase is in the range of about 80:20 to 30:70.

3. The composition according to claim 1 wherein said organic phase comprises an alkane, cycloalkane, cycloalkanone, or cycloalcohol containing 6 to 20 carbon atoms.

4. The composition according to claim 1 wherein said aqueous phase comprises one or more components selected from the group consisting of polyethylene glycol, polyvinyl pyrrolidone, dextran, mannitol, sucrose, trehalose, lactose, sorbitol, an amino acid, a water soluble protein, a poloxamer surfactant, a polyoxyalkylene fatty acid ester surfactant, a polyoxyethylene ester surfactant, and a polyoxyethylene ether surfactant.

5. A composition according to any one of claims 1 through 4 wherein said microparticles comprise gelatin, albumin, collagen, polycaprolactone, polylactide, polyglycolide or copolymers of lactide and glycolide.

6. A composition according to claim 5 wherein said microparticles comprise capsules having an outer shell and an inner core.

7. A lyophilized product prepared by freeze drying a composition of claim 6.

8. A lyophilized product prepared by freeze drying a composition of claim 5.

9. A lyophilized product prepared by freeze drying a composition of any of claims 1 through 4.

10. A process for forming a lyophilized composition of microparticles comprising the steps of:
    (a) freezing a composition according to any of claims 1 through 4;
    (b) drying in vacuo the frozen composition from step (a) to remove said organic phase.

11. A process according to claim 10 wherein said biocompatable materials comprise gelatin, albumin, collagen, polycaprolactone, polylactide, polyglycolide or copolymers of lactide and glycolide.

12. A process according to claim 10 wherein said microparticles comprise capsules having an outer shell and an inner core.

13. A composition according to claim 1, wherein the microparticles comprise water-insoluble microparticles.

14. A composition according to claim 1, wherein the microparticles are suspended in the aqueous phase.

15. A method of preparing a composition for delivery of a therapeutic or diagnostic material, the method comprising:
    forming an oil-in-water emulsion comprising an aqueous phase and an organic phase, the organic phase having a freezing point of about or higher than the freezing point of the aqueous phase;
    mixing a plurality of microparticles in the emulsion to form a suspension, the microparticles comprising a therapeutic or diagnostic material;
    freezing the suspension; and
    drying the frozen suspension in vacuo to substantially remove the organic phase.

* * * * *